United States Patent
Harth et al.

(10) Patent No.: US 6,900,363 B2
(45) Date of Patent: May 31, 2005

(54) METHOD FOR THE PRODUCTION OF 1,2-DICHLOROETHANE

(75) Inventors: Klaus Harth, Altleiningen (DE); Götz-Peter Schindler, Mannheim (DE); Christian Walsdorff, Ludwigshafen (DE); Christian Kuhrs, Heidelberg (DE); Falk Simon, Bürstadt-Riedrode (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/497,598

(22) PCT Filed: Dec. 4, 2002

(86) PCT No.: PCT/EP02/13729

§ 371 (c)(1),
(2), (4) Date: Jun. 3, 2004

(87) PCT Pub. No.: WO03/048088

PCT Pub. Date: Jun. 12, 2003

(65) Prior Publication Data

US 2004/0267063 A1 Dec. 30, 2004

(30) Foreign Application Priority Data

Dec. 5, 2001 (DE) .......................................... 101 59 615

(51) Int. Cl.[7] .............................................. C07C 17/15
(52) U.S. Cl. ..................... 570/223; 570/220; 570/245
(58) Field of Search ................................ 570/223, 220, 570/245

(56) References Cited

U.S. PATENT DOCUMENTS 3,658,933 A * 4/1972 Beard .......................... 585/657
3,658,934 A * 4/1972 Beard .......................... 585/657
3,702,311 A * 11/1972 Beard .......................... 502/225
3,987,119 A * 10/1976 Kurtz et al. ................. 570/223
4,172,099 A * 10/1979 Severino ..................... 570/223

FOREIGN PATENT DOCUMENTS

| DE | 1 443 707 | 11/1968 |
| GB | 970961 | 9/1964 |
| WO | 95/07249 | 3/1995 |
| WO | 00/26164 | 3/2000 |

OTHER PUBLICATIONS

Derwent Abst. 2000–365532/31.

* cited by examiner

Primary Examiner—Michael L. Shippen
(74) Attorney, Agent, or Firm—Novak Druce & Quigg, LLP

(57) ABSTRACT

A process for preparing 1,2-dichloroethane which comprises
(A) feeding an ethane-containing feed gas stream into a dehydrogenation zone and dehydrogenating ethane to ethane to give a product gas stream comprising ethane, ethane and secondary constituents,
(B) feeding the ethan- and ethene-containing dehydrogenation product gas stream as a single stream or a plurality of substreams, optionally after having separated off secondary constituents, into one or more chlorination zones, chlorinating ethene to 1,2-dichloroethane to give one or more product gas streams comprising 1,2-dichloroethane, ethane and possibly further secondary constituents, isolating 1,2-dichloroethane and one or more ethane-containing circulating gas streams and recirculating the ethane-containing circulating gas stream or streams to the ethane dehydrogenation.

10 Claims, 3 Drawing Sheets

METHOD FOR THE PRODUCTION OF 1,2-DICHLOROETHANE

Figure 1:
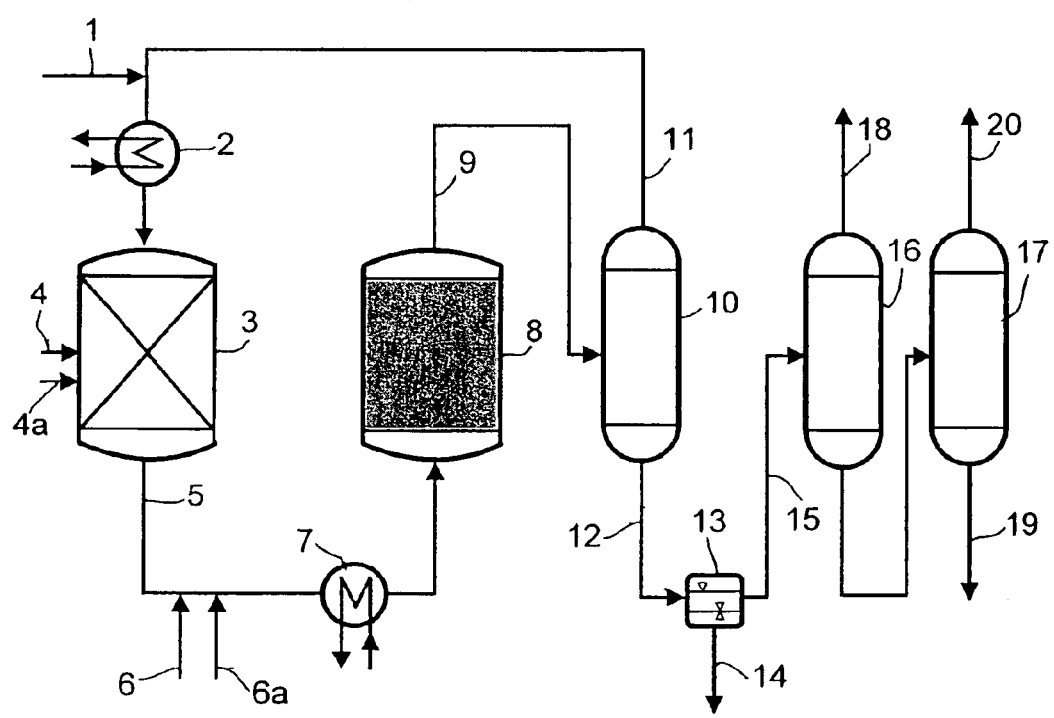

The present invention relates to a process for preparing 1,2-dichloroethane.

1,2-Dichloroethane is prepared by oxychlorination of ethene using HCl and oxygen or by direct chlorination of ethene by means of chlorine. 1,2-dichloroethane is predominantly processed further by pyrolysis to give vinyl chloride, resulting in liberation of HCl. Oxychlorination and direct chlorination are usually carried out in parallel and the hydrogen chloride obtained in the dichloroethane pyrolysis is used in the oxychlorination.

Ethene is prepared predominantly by thermal cracking of saturated hydrocarbons. This gives a hydrocarbon mixture comprising methane, ethane, ethene, acetylene, propane, propene, butenes, butadiene, $C_5$- and higher hydrocarbons. The gases from the cracker have to be subjected to a multistep work-up before the pure end products are obtained. The separation of ethane and ethene requires columns having from 80 to 100 trays.

Since ethene and propene are generally obtained together in the cracking of naphtha, the amount of one product produced is always coupled to the amount of the other product produced.

Ethene can also be obtained by dehydrogenation of ethane or from refinery gases. Here, the isolation of ethene requires the complicated and energy-intensive separation of ethene from unreacted ethane and by-products.

1,2-Dichloroethane can be prepared by chlorination of ethene. The chlorination can either be carried out as a direct chlorination by means of chlorine or as an oxychlorination by means of hydrogen chloride and oxygen.

1,2-Dichloroethane is predominantly processed further by elimination of hydrogen chloride to give vinyl chloride. Furthermore, the oxychlorination of ethene is important in the chemical industry since it provides a cost-effective further use for hydrogen chloride from processes in which hydrogen chloride is obtained as coproduct, for example phosgene-based processes for preparing isocyanates.

The processes known from the prior art for preparing 1,2-dichloroethane from ethene are encumbered by the high costs of the ethene starting material.

Processes in which vinyl chloride is obtained by oxychlorination of ethane are also known. Such a process is described, for example, in WO 95/07249. However, the EVC process described there has the disadvantage that it requires three different reactor stages and is thus complicated. In addition, the source of chlorine used is relatively expensive elemental chlorine ($Cl_2$), so that the process offers no opportunity for utilizing hydrogen chloride obtained in other processes. Finally, this process has to be carried out at temperatures significantly higher than those in the oxychlorination of ethene, which considerably increases the risk of formation of dioxins because of the copper-containing catalysts used.

None of the processes for the oxychlorination of ethane to give vinyl chloride can be carried out in existing plants for the preparation of vinyl chloride from ethene and they therefore make comprehensive new capital investments necessary.

It is an object of the invention to place the preparation of 1,2-dichloroethane and the downstream product vinyl chloride on a new raw material basis. In particular, it is an object of the invention to provide a process for preparing 1,2-dichloroethane or vinyl chloride which uses ethane as raw material and which can be implemented by modification of existing processes for preparing 1,2-dichloroethane or vinyl chloride from ethylene as raw material.

We have found that this object is achieved by a process for preparing 1,2-dichloroethane which comprises
(A) feeding an ethane-containing feed gas stream into a dehydrogenation zone and dehydrogenating ethane to ethene to give a product gas stream comprising ethane, ethene and secondary constituents,
(B) feeding the ethane- and ethene-containing dehydrogenation product gas stream as a single stream or a plurality of substreams, optionally after having separated off secondary constituents, into one or more chlorination zones, chlorinating ethene to 1,2-dichloroethane to give one or more product gas streams comprising 1,2-dichloroethane, ethane and possibly further secondary constituents, isolating 1,2-dichloroethane and one or more ethane-containing circulating gas streams and recirculating the ethane-containing circulating gas stream or streams to the ethane dehydrogenation.

The process of the present invention can readily be implemented by modification of existing plants for preparing 1,2-dichloroethane from ethene. In the present process, ethene is obtained by dehydrogenation of ethane in a stage preceding the ethene chlorination, the ethene chlorination is carried out in the presence of unreacted ethane and possibly further secondary constituents from the ethane dehydrogenation and the unreacted ethane is returned as circulating gas to the ethane dehydrogenation.

In a first part (A) of the process, ethane is dehydrogenated to ethene.

The dehydrogenation of ethane to ethene can be carried out by thermal cracking of ethane. This gives, for example, a product gas mixture comprising 2.7% by weight of hydrogen, 9.5% by weight of methane, 58.5% by weight of ethene, 23.2% by weight of ethane, 2.3% by weight of propene and 3.8% by weight of $C_4^+$-hydrocarbons.

Ethane can be dehydrogenated to ethene by oxidative dehydrogenation.

The oxidative dehydrogenation of ethane can, for example, be carried out as described in U.S. Pat. No. 4,250,346 over Mo/V mixed oxide catalysts or as described in WO 00/48971 over NiO-containing catalysts at from 300 to 500° C. and ethane conversions of from 10 to 20%.

The alkane dehydrogenation is preferably carried out as a nonoxidative catalytic dehydrogenation. Here, ethane is partly dehydrogenated to ethene over a dehydro-genation-active catalyst in a dehydrogenation reactor. In the dehydrogenation, not only hydrogen but also small amounts of methane are formed as cracking products of ethane. In addition, depending on the way in which the dehydrogenation is carried out, carbon oxides (CO, $CO_2$), water and nitrogen can be present in the product gas mixture from the ethane dehydrogenation. Unreacted ethane is also present in the product gas mixture.

The catalytic ethane dehydrogenation can be carried out with or without oxygen-containing gas as cofeed.

The catalytic ethane dehydrogenation can in principle be carried out using all types of reactor and modes of operation known from the prior art. A comparatively comprehensive description of dehydrogenation processes which are suitable for the purposes of the present invention is given in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable type of reactor is a fixed-bed tube reactor or a shell-and-tube reactor. In these, the catalyst (dehydrogenation catalyst and, when employing oxygen as cofeed, optionally a specific oxidation catalyst) is present as a fixed bed in a reaction tube or in a bundle of reaction tubes. The reaction tubes are usually heated indirectly by a gas, e.g. a hydrocarbon such as methane, being burnt in the space surrounding the reaction tubes. It is advantageous to apply this indirect form of heating only to the first about 20 to 30% of the length of the fixed bed and to heat the remaining length of the bed to the required reaction temperature by means of the radiant heat liberated in the course of the indirect heating. Customary internal reaction tube diameters are from about 10 to 15 cm. A typical shell-and-tube reactor employed for dehydrogenation has from about 300 to 1000 reaction tubes. The temperature in the interior of the reaction tubes is usually in the range from 300 to 1200° C., preferably in the range from 600 to 1000° C. The working pressure is usually from 0.5 to 8 bar, frequently from 1 to 2 bar when using a low level of steam dilution (analogous to the BASF-Linde process for propane dehydrogenation), but also from 3 to 8 bar when using high steam dilution (analogous to the "steam active reforming process" (STAR process) of Phillips Petroleum Co. for the dehydrogenation of propane or butane, cf. U.S. Pat. Nos. 4,902,849, 4,996,387 and 5,389,342). Typical space velocities over the catalyst (GSHV) are from 500 to 2 000 $h^{-1}$. The catalyst geometry can be, for example, spherical or cylindrical (hollow or solid).

The catalytic ethane dehydrogenation can also, as described in Chem. Eng. Sci. 1992 b, 47 (9–11), 2313, be carried out in the presence of a heterogeneous catalyst in a fluidized bed, with the ethane not being diluted. It is advantageous to operate two fluidized beds side-by-side, with one of these generally being in the state of regeneration. The working pressure is typically from 1 to 2 bar, and the dehydrogenation temperature is generally from 550 to 600° C. The heat required for the dehydrogenation is introduced into the reaction system by preheating the dehydrogenation catalyst to the reaction temperature. Mixing-in an oxygen-containing cofeed can make it possible to omit the preheater and to generate the necessary heat directly in the reactor system by combustion of hydrogen in the presence of oxygen. If desired, a hydrogen-containing cofeed can additionally be mixed in.

The catalytic ethane dehydrogenation can be carried out in a tray reactor. This contains one or more superposed catalyst beds. The number of catalyst beds can be from 1 to 20, advantageously from 1 to 6, preferably from 1 to 4 and in particular from 1 to 3. The reaction gas preferably flows through the catalyst beds radially or axially. In general, such a tray reactor is operated using a fixed catalyst bed. In the simplest case, the fixed catalyst beds are arranged axially in a shaft furnace reactor or in the annular gaps of concentric cylindrical gratings. One shaft furnace reactor corresponds to one tray. In a preferred embodiment, the dehydrogenation is carried out in a single shaft furnace reactor. In a further preferred embodiment, the dehydrogenation is carried out in a tray reactor containing 3 catalyst beds. When a mode of operation without oxygen as cofeed is employed, the reaction gas mixture is subjected in the tray reactor to intermediate heating on its way from one catalyst bed to the next catalyst bed, e.g. by passing over heat exchanger surfaces heated by means of hot gases or by passing through tubes heated by means of hot combustion gases.

In a preferred embodiment of the process of the present invention, the catalytic ethane dehydrogenation is carried out autothermally. For this purpose, oxygen is additionally mixed into the reaction gas mixture of the ethane dehydrogenation in at least one reaction zone and the hydrogen present in the reaction gas mixture is burnt, thus generating at least part of the necessary heat of dehydrogenation directly in the reaction gas mixture in the reaction zone or zones. A feature of autothermal operation compared to oxidative operation is, for example, the presence of hydrogen in the output gas. In the oxidative method, no significant amounts of free hydrogen are formed.

In general, the amount of oxygen-containing gas added to the reaction gas mixture is selected so that the combustion of the hydrogen present in the reaction gas mixture and any hydrocarbons present in the reaction gas mixture and/or carbon present in the form of carbon deposits generates the quantity of heat required for the dehydrogenation of the ethane. In general, the total amount of oxygen introduced is, based on the total amount of ethane, from 0.001 to 0.5 mol/mol, preferably from 0.005 to 0.2 mol/mol, particularly preferably from 0.05 to 0.2 mol/mol. Oxygen can be used either as pure oxygen or as oxygen-containing gas in admixture with inert gases. A preferred oxygen-containing gas is air. The inert gases and the resulting combustion gases generally have an additional diluting effect and thus promote the heterogeneously catalyzed dehydrogenation.

The ethane dehydrogenation can also be carried out autothermally at about 1000° C. and a contact time of a few ms over a platinum catalyst. For example, at an ethane conversion of about 70%, ethene selectivities of about 65% are achieved, about 25% of the ethane reacted are oxidized to CO and $CO_2$, about 5% are converted into methane and about 5% are converted into higher hydrocarbons such as propane and propene. The use of a platinum/tin catalyst in place of platinum alone increases the ethene selectivity to about 70% (Chem. Eng. Sci. 54 (1999) 765–773). The oxidative ethane dehydrogenation can also be carried out with introduction of hydrogen, preferably in an ($H_2$:$O_2$) ratio of 2:1, e.g. in the presence of platinum/tin/aluminum oxide catalysts. In this case, the ethene selectivity is increased to about 85% (Beretta, Chem. Eng. Sci. 1999, 54, 765–773; L. D. Schmidt et al. American Institute of Chemical Engineers Journal 2000, Vol. 46 (8) 1492–1495).

The hydrogen burnt to generate heat is the hydrogen formed in the catalytic ethane dehydrogenation together with any additional hydrogen added to the reaction gas mixture. Preference is given to the amount of hydrogen present being such that the $H_2/O_2$ molar ratio in the reaction gas mixture directly after the introduction of oxygen is from 2 to 10 mol/mol. In the case of multistage reactors, this applies to each intermediate introduction of oxygen and, if desired, hydrogen.

The combustion of hydrogen occurs catalytically. The dehydrogenation catalyst used generally also catalyzes the combustion of hydrocarbons and of hydrogen by means of oxygen, so that no further specific oxidation catalyst is necessary in principle. In one embodiment, the dehydrogenation is carried out in the presence of one or more oxidation catalysts which selectively catalyze the combustion of hydrogen by means of oxygen in the presence of ethane and ethene. The combustion of these hydrocarbons by means of oxygen to form CO and $CO_2$ proceeds to only a minor extent as a result, which has a significant positive effect on the selectivities to ethene. The dehydrogenation catalyst and the oxidation catalyst are preferably present in different reaction zones.

In the case of a multistage reaction, the oxidation can be present in only one, in a plurality of or in all reaction zone(s).

The catalyst which selectively catalyzes the oxidation of hydrogen is preferably located in places at which the oxygen partial pressures are higher than at other points in the reactor, in particular in the vicinity of the feed point for the oxygen-containing gas. The introduction of oxygen-containing gas and/or hydrogen can be carried out at one or more points on the reactor.

In one embodiment of the process of the present invention, intermediate introduction of oxygen-containing gas and of hydrogen is carried out upstream of each tray of a tray reactor. In a further embodiment of the process of the present invention, the introduction of oxygen-containing gas and of hydrogen is carried out upstream of each tray apart from the first tray. In one embodiment, a bed of a specific oxidation catalyst is present downstream of each feed point, followed by a bed of the dehydrogenation catalyst. In a further embodiment, no specific oxidation catalyst is present. The dehydrogenation temperature is generally from 400 to 1100° C., and the pressure in the last catalyst bed of the tray reactor is generally from 0.2 to 5 bar, preferably from 1 to 3 bar. The space velocity (GSHV) is generally from 500 to 2000 $h^{-1}$, and in high-load operation may also be up to 100 000 $h^{-1}$, preferably from 4 000 to 16 000 $h^{-1}$.

A preferred catalyst which selectively catalyzes the combustion of hydrogen comprises oxides or phosphates selected from the group consisting of oxides or phosphates of germanium, tin, lead, arsenic, antimony or bismuth. A further preferred catalyst which catalyzes the combustion of hydrogen comprises a noble metal of transition group VIII or I.

The dehydrogenation catalysts used generally comprise a support and an active composition. The support comprises a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof as support. The mixtures can be physical mixtures or chemical mixed phases such as magnesium or zinc aluminum oxide mixed structures. Preferred supports are zirconium dioxide and/or silicon dioxide, particularly preferably mixtures of zirconium dioxide and silicon dioxide.

The active composition of the dehydrogenation catalysts generally comprises one or more elements of transition group VIII, preferably platinum and/or palladium, particularly preferably platinum. The dehydrogenation catalysts may further comprise one or more elements of main group I and/or II, preferably potassium and/or cesium. In addition, the dehydrogenation catalysts may further comprise one or more elements of transition group III including the lanthanides and actinides, preferably lanthanum and/or cerium. Finally, the dehydrogenation catalysts may further comprise one or more elements of main group III and/or IV, preferably one or more elements selected from the group consisting of boron, gallium, silicon, germanium, tin and lead, particularly preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all the dehydrogenation catalysts disclosed in WO 99/46039, U.S. Pat. No. 4,788,371, EP-A 705 136, WO 99/29420, U.S. Pat. Nos. 5,220,091, 5,430,220, 5,877,369, EP 0 117 146, DE-A 199 37 106, DE-A 199 37 105 and DE-A 199 37 107 can be used for the purposes of the present invention. Particularly preferred catalysts for the above-described variants of the autothermal ethane dehydrogenation (step A) are the catalysts described in Examples 1, 2, 3 and 4 of DE-A 199 37 107.

The ethane dehydrogenation is preferably carried out in the presence of steam. The steam added serves as heat transfer medium and aids the gasification of organic deposits on the catalysts, thus countering carbonization of the catalysts and increasing the operating life of the catalyst. The organic deposits are in this way converted into carbon monoxide and carbon dioxide.

The dehydrogenation catalyst can be regenerated in a manner known per se. Thus, steam can be added to the reaction gas mixture or an oxygen-containing gas can be passed at elevated temperature over the catalyst bed from time to time so as to burn off the deposited carbon.

The ethane used in the ethane dehydrogenation does not have to be chemically pure. For example, the ethane used can contain up to 50% by volume of further gases such as methane, propane, propene, propyne, acetylene, $H_2S$, $SO_2$, butanes, butenes and traces of organic nitrogen or sulfur compounds. The crude ethane used generally contains at least 90% by volume, preferably at least 95% by volume and particularly preferably at least 98% by volume, of ethane. If desired, ethane can be separated off from higher-boiling secondary components by absorption, extraction or distillation in a deethanizer.

The ethane dehydrogenation gives a gas mixture comprising ethene and unreacted ethane together with secondary constituents. Usual secondary constituents are methane, hydrogen, water, nitrogen, CO and $CO_2$. The composition of the gas mixture leaving the dehydrogenation stage can vary greatly depending on the mode of operation of the dehydrogenation. Thus, when the preferred autothermal dehydrogenation with introduction of oxygen and additional hydrogen is carried out, the product gas mixture will have a comparatively high content of water and carbon oxides. In the case of modes of operation without introduction of oxygen, the product gas mixture from the dehydrogenation will have a comparatively high hydrogen content.

For example, in the case of the dehydrogenation of ethane, the product gas mixture leaving the dehydrogenation reactor comprises at least the constituents ethane, ethene and molecular hydrogen. Furthermore, it will generally further comprise $N_2$, $H_2O$, methane, CO and $CO_2$. It will usually be under a pressure of from 0.3 to 10 bar and frequently have a temperature of from 400 to 1200° C., in favorable cases from 500 to 800° C.

The product gas stream from the autothermal ethane dehydrogenation typically comprises from 10 to 70% by volume of ethane, from 5 to 60% by volume of ethene, from 0 to 20% by volume of hydrogen, from 5 to 50% by volume of water vapor, from 0 to 50% by volume of methane and from 0 to 20% by volume of carbon oxides.

If desired, hydrogen can be removed from the product gas mixture from the ethane dehydrogenation by combustion in the presence of added oxygen or air, preferably oxygen, and the presence of a suitable selective oxidation catalyst.

In a part (B) of the process, the ethane- and ethene-containing dehydrogenation product gas stream is fed as a single stream or a plurality of substreams into one or more chlorination zones and ethene is chlorinated to give 1,2-dichloroethane.

The ethene chlorination can be carried out as an oxychlorination or as a direct chlorination. Oxychlorination and direct chlorination can also be carried out in parallel.

The ethene chlorination can be carried out as an oxychlorination. The product gas stream fed into the oxychlorination zone comprises ethene and unreacted ethane together with, preferably, all secondary constituents from the ethane dehydrogenation.

As a result of the dilution of ethene with ethane and the secondary constituents in the feed gas stream to the oxychlorination, a higher selectivity of 1,2-dichloroethane formation, based on ethene used, is achieved and a smaller amount of chlorinated by-products and carbon oxides is formed.

The oxychlorination of ethene to 1,2-dichloroethane can in principle be carried out using all reactor types and modes of operation known from the prior art.

The oxychlorination of ethene is generally carried out in the gas phase in the presence of a supported catalyst comprising copper(II) chloride in a fixed-bed or fluidized-bed reactor. The oxychlorination reaction can be carried out with introduction of additional oxygen or air. It is preferably carried out with introduction of pure oxygen. Otherwise, the reaction results in formation of large amounts of nitrogen which have to be discharged from the process and are difficult to free of entrained organochlorine compounds. The formation of "hot spots" in the oxychlorination reactor is also avoided more easily by employing pure oxygen. The hydrogen chloride:oxygen ($HCl:O_2$) molar ratio is generally from 5:1 to 3:1, preferably from 4.5:1 to 3.2:1, in particular from 3.99:1 to 3.5:1. The ethylene:HCl molar ratio is generally about 1:2. Hydrogen chloride is preferably present in a slightly substoichiometric amount based on the reaction $2C_2H_4+4HCl+O_2 \rightarrow 2C_2H_4Cl_2+2H_2O$, so that it is ensured that hydrogen chloride is virtually completely reacted in one pass through the reactor. Furthermore, the ethylene:HCl:$O_2$ ratio is preferably selected so that ethylene is also very substantially reacted in one pass through the reactor. The ratio of hydrocarbons (ethane, ethene and possibly methane) to oxygen should be such that a rich reaction mixture above the explosive limit is present. The (ethene+ethane):HCl:$O_2$ molar ratio can, for example in a fluidized-bed process without appreciable proportions of further hydrocarbons, be 1:1.19:0.31 or 1:0.71:1.8.

Suitable catalysts generally comprise a copper compound, preferably a copper chloride or a copper compound which is entirely or partly converted into a copper chloride under the reaction conditions, on a support. Preferred supports are aluminum oxides, for example $\gamma$-$Al_2O_3$. The catalysts can further comprise promoters such as alkali metal chlorides, in particular KCl, alkaline earth metal chlorides, in particular $MgCl_2$, or chlorides of the rare earth metals, in particular $CeCl_3$. The oxychlorination is generally carried out at from 200 to 300° C. and pressures of from 2.5 to 7 bar. The HCl conversion is typically from 95 to 99.9%.

Fixed-bed processes for the oxychlorination of ethene to form 1,2-dichloroethane are described, for example, in DE-A 100 03 510, U.S. Pat. No. 4,206,180 and GB-A 2,298,197. Catalysts for the oxychlorination of ethene to form 1,2-dichloroethane in fixed-bed processes are described, for example, in EP-A 1 127 618, U.S. Pat. No. 4,366,093 and EP-A 1 053 789.

Fluidized-bed processes for the oxychlorination of ethene to form 1,2-dichloro-ethane are described, for example, in DE-A 197 53 165 A1, EP-A 1 023 939 and EP-A 0 029 143. Catalysts for the oxychlorination of ethene to form 1,2-dichloro-ethane in fluidized-bed processes are described, for example, in EP-A 0 582 165, EP-A 0 375 202 and EP-A 0 657 212.

The oxychlorination can also be carried out, as described in DE-A 100 03 510, over a fixed catalyst bed which contains no separate inert material for dilution.

The product gas stream from the oxychlorination comprises 1,2-dichloroethane, ethane, water, generally traces of hydrogen chloride, ethene and oxygen and also by-products of the oxychlorination, e.g. carbon dioxide, carbon monoxide and chlorinated by-products such as chloral, vinyl chloride, 1,2-dichloroethene, chloroethane, 1,1-dichloroethane, 1,1,2-trichloroethane, tetrachloroethane, chloro-form and carbon tetrachloride. Based on ethylene reacted, generally not more than 4%, preferably not more than 1.5%, of chlorinated by-products and generally not more than 5%, preferably not more than 2%, of carbon oxides are formed. In addition, the product gas stream can further comprise other secondary constituents originating from the ethane dehydrogenation, for example methane, hydrogen, nitrogen and additional amounts of oxygen, CO and $CO_2$.

1,2-Dichloroethane and an ethane-containing gas stream are obtained from the product gas stream from the oxychlorination and the ethane-containing gas stream is recirculated as circulating gas to the ethane dehydrogenation. For this purpose, the condensable components of the product gas stream, which comprise 1,2-dichloroethane, water and hydrogen chloride together with chlorinated secondary constituents, are condensed out. The condensation step is usually carried out at from 10 to 100° C. and a pressure of from 2 to 5 bar. The condensation is preferably carried out in two steps in two successive quenching towers ("hot" and "cold") with addition of dilute aqueous sodium hydroxide for neutralization of unreacted hydrogen chloride in the second quenching tower. An aqueous condensate phase which is slightly acidic with hydrochloric acid and an organic condensate phase are obtained and are separated in a phase separator. The aqueous phase is neutralized if appropriate and discharged from the process. The organic phase is distilled, for example in a series of two distillation columns, with low boilers being separated off at the top of a first column and pure 1,2-dichloroethane being separated off at the top of a second column.

The gas stream comprising ethane and the incondensable secondary constituents can be recirculated without separation of the secondary constituents as an ethane-containing circulating gas stream to the ethane dehydrogenation. The circulating gas stream generally further comprises carbon oxides and small amounts of ethene and/or oxygen and also traces of chlorinated organic by-products of the oxychlorination which have not been completely condensed out, for example vinyl chloride. The concentration of these chlorinated secondary constituents in the circulating gas stream is generally from 10 to 10 000 ppm. The circulating gas stream can further comprise hydrogen, methane and/or (when using air instead of oxygen) nitrogen and also further inert secondary constituents (argon) from the ethane dehydrogenation and/or the oxychlorination. To prevent these constituents which are completely inert under the process conditions from accumulating in the circulating gas, they can be discharged from the process via a purge stream.

In one embodiment of the process of the present invention, therefore, a circulating gas stream comprising ethane and incondensable secondary constituents selected from the group consisting of ethene, methane, carbon oxides, oxygen, nitrogen and hydrogen, possibly together with traces of organic chlorine compounds, is separated off from the product gas stream from the oxychlorination and is recirculated to the ethane dehydrogenation.

In an embodiment of the process of the present invention, carbon dioxide is separated off from the circulating gas stream by means of a $CO_2$ gas scrub. The carbon dioxide gas scrub can be preceded by a separate combustion stage in which carbon monoxide is selectively oxidized to carbon dioxide, preferably in the presence of residual oxygen present in the circulating gas stream.

In the case of autothermal operation of the ethane dehydrogenation, any methane or chlorinated hydrocarbons present can be oxidized via carbon monoxide to carbon dioxide and the oxidation product carbon dioxide can be removed from the process circuit by means of the $CO_2$ gas scrub.

In a further embodiment of the process, separation of secondary constituents from a stream consisting essentially of ethane can also be carried out by means of other customary separation methods such as distillation, rectification, membrane processes or adsorption. In a preferred embodiment of the process of the present invention, an ethane-containing gas stream is separated off from the gas stream comprising incondensable components by means of a high-boiling absorption medium in an absorption/desorption cycle and this ethane-containing gas stream is recirculated as circulating gas stream to the ethane dehydrogenation stage. In this way, virtually all incondensable secondary constituents (nitrogen, argon, hydrogen, methane, carbon oxides, oxygen) are removed from the process circuit. For this purpose, the ethane is absorbed in an inert absorption medium in an absorption stage, giving an ethane-laden absorption medium and an offgas comprising the other secondary constituents. Ethane is liberated again from the absorption medium in a desorption stage.

Inert absorption media used in the absorption stage are generally high-boiling nonpolar solvents in which the alkane/alkene mixture to be separated off has a significantly higher solubility than have the other constituents of the product gas mixture. Absorption can be carried out simply by passing the product gas mixture through the absorption medium. However, it can also be carried out in columns or in rotary absorbers. These can be operated in cocurrent, countercurrent or in crossflow. Suitable absorption columns are, for example, tray columns having bubble cap trays, centrifugal trays and/or sieve trays, columns containing structured packing, e.g. sheet metal packing having a specific surface area of from 100 to 1000 $m^2/m^3$, e.g. Mellapak® 250 Y, and columns packed with random packing elements. It is also possible to use trickle towers and spray towers, graphite block absorbers, surface absorbers such as thick film and thin film absorbers and rotary columns, pan scrubbers, cross-spray scrubbers and rotary scrubbers.

Suitable absorption media are comparatively nonpolar organic solvents, for example aliphatic $C_8$- to $C_{18}$-alkenes or aromatic hydrocarbons, e.g. the middle oil fractions from paraffin distillation, or ethers having bulky groups or mixtures of these solvents. It is possible to add a polar solvent such as dimethyl phthalate to these. Further suitable absorption media are esters of benzoic acid and phthalic acid with straight-chain $C_1$-$C_8$-alkanols, e.g. n-butyl benzoate, methyl benzoate, ethyl benzoate, dimethyl phthalate, diethyl phthalate, and also heat transfer oils such as biphenyl and diphenyl ether, their chloro derivatives and triarylalkenes. One suitable absorption medium is a mixture of biphenyl and diphenyl ether, preferably having the azeotropic composition, for example the commercially available Diphyl®. This solvent mixture frequently contains from 0.1 to 25% by weight of dimethyl phthalate. Other suitable absorption media are octanes, nonanes, decanes, undecanes, dodecanes, tridecanes, tetradecanes, pentadecanes, hexadecanes, heptadecanes and octadecanes or fractions which comprise the abovementioned linear alkanes as main components and are obtained from refinery streams.

For desorption, the loaded absorption medium is heated and/or depressurized to a lower pressure. Alternatively, desorption can also be carried out by stripping or a combination of depressurization, heating and stripping in one or more process steps. The absorption medium which has been regenerated in the desorption stage is returned to the absorption stage.

The absorption/desorption cycle gives a circulating gas stream which consists essentially of ethane when the absorption/desorption cycle is carried out after chlorination and before (renewed) dehydrogenation, and consists essentially of ethane and ethene when the absorption/desorption cycle is carried out after dehydrogenation and before chlorination. In general, this circulating gas stream also contains traces of chlorinated organic by-products such as vinyl chloride, generally in amounts of from 10 to 10 000 ppm.

Surprisingly, the organic chlorine compounds in the circulating gas recirculated to the ethane dehydrogenation result in an increase in the activity and the operating life of the dehydrogenation catalyst.

In a further embodiment of the process of the present invention, a gas stream comprising ethane and incondensable secondary constituents selected from the group consisting of ethene, methane, carbon oxides, oxygen, nitrogen, hydrogen and traces of organic chlorine compounds is separated off from the product gas stream from the oxychlorination, a circulating gas stream which consists essentially of ethane and can also contain traces of organic chlorine compounds is separated off from this circulating gas stream by means of a high-boiling absorption medium in an absorption/desorption cycle and this circulating gas stream is recirculated to the ethane dehydrogenation stage.

The chlorination can be carried out as a direct chlorination.

The secondary constituents originating from the feed gas stream to the ethane dehydrogenation and those formed in the ethane dehydrogenation can be separated off from the feed gas stream to the direct chlorination prior to the direct chlorination.

To separate off the hydrogen present in the product gas mixture from the ethane dehydrogenation, the product gas mixture can be passed, if appropriate after cooling, for example in an indirect heat exchanger, over a membrane which is permeable only to molecular hydrogen and is generally configured as a tube. The molecular hydrogen which has been separated off in this way can, if required, be at least partly used in the dehydrogenation or else can be passed to another use, for example for the generation of electric energy in fuel cells.

As an alternative, the hydrogen can be separated off by partial condensation, adsorption and/or rectification, preferably under superatmospheric pressure.

Hydrogen can also, as described above, be selectively burnt over a suitable catalyst.

Hydrogen can also be separated off from the product gas mixture from the ethane dehydrogenation together with further secondary constituents.

It can be necessary to separate off hydrogen to avoid the formation of explosive hydrogen/oxygen or hydrogen/chlorine gas mixtures in the direct chlorination.

In one embodiment of the process of the present invention, water is firstly separated off. The removal of water prior to the direct chlorination can be advantageous in order to avoid an adverse effect on the catalyst used in the direct chlorination and/or in order to avoid formation of an aqueous phase in the work-up of the products from the direct chlorination. The removal of the water can be achieved by, for example, condensation by cooling and/or compression of the product gas stream from the dehydrogenation and can be carried out in one or more cooling and/or compression stages. The removal of water is usually carried out when the alkane dehydrogenation is carried out autothermally or is carried out isothermally with introduction of steam (in a manner analogous to the Linde or STAR process for the dehydrogenation of propane) and the product gas stream consequently has a high water content.

After removal of the water, ethane and ethene can be separated off from the other secondary constituents by means of a high-boiling absorption medium in an absorption/desorption cycle. Here, ethane and ethene are absorbed in an inert absorption medium in an absorption stage to give an absorption medium laden with ethane and ethene and an offgas comprising the secondary constituents, and ethane and ethene are liberated from the absorption medium in a desorption stage.

The separation of essentially all secondary constituents other than ethane and ethene from the product gas mixture is preferably achieved by bringing the product gas mixture which has been cooled to from 10 to 70° C. into contact with a preferably high-boiling nonpolar organic solvent in which ethane and ethene are absorbed at a pressure of generally from 0.1 to 50 bar, preferably from 2 to 20 bar, and a temperature of generally from 0 to 100° C., preferably from 5 to 80° C. After desorption, preferably by means of stripping, ethane and ethene are liberated again and are passed to the direct chlorination.

The absorption/desorption cycle is otherwise carried out as described above, preferably using the abovementioned high-boiling absorption media. Preference is given to carrying out both absorption/desorption cycles, i.e. firstly the separation of the secondary constituents from the product gas stream from the oxychlorination and secondly separation of the secondary constituents from the product gas stream from the ethane dehydrogenation, using a common solvent circuit.

The direct chlorination of ethene by means of chlorine to form 1,2-dichloroethane can in principle be carried out using all known types of reactor and all known modes of operation. A process suitable for preparing 1,2-dichloroethane by direct chlorination is described, for example, in U.S. Pat. No. 4,873,384.

The direct chlorination can be carried out in the liquid phase, and is preferably carried out in this way. The direct chlorination can be carried out as a high-temperature direct chlorination in the presence of $FeCl_3$ as homogeneous catalyst in 1,2-dichloroethane as reaction medium at from 120 to 130° C. and a pressure of about 3 bar. For this purpose, chlorine and the ethane/ethene mixture, which may contain secondary constituents, are introduced into the liquid reaction medium. The ethene:chlorine molar ratio is usually close to 1, with ethene being present in a slight excess so that the ratio is, for example, in the range from 1.01:1 to 1.1:1. The direct chlorination can also be carried out as a low-temperature direct chlorination in the presence of a metal complex as catalyst in 1,2-dichloroethane. The heat of reaction liberated causes vaporization of part of the reaction medium. The direct chlorination can also be carried out as a gas-phase direct chlorination at about 250° C. and 1.4 bar over an aluminum oxide catalyst in a fluidized bed.

The ethene conversion in the direct chlorination is generally close to 99%, and the chlorine conversion is close to 100%. The selectivity of the 1,2-dichloroethane formation is generally about 99%. The direct chlorination is preferably carried out in the presence of small amounts of oxygen to suppress the formation of chlorinated by-products.

The product gas stream from the direct chlorination comprises 1,2-dichloroethane, ethane and possibly further secondary constituents. 1,2-Dichloroethane and an ethane-containing circulating gas stream are obtained from this product gas stream and the ethane-containing circulating gas stream is recirculated to the ethane dehydrogenation.

To isolate 1,2-dichloroethane, the condensable components of the product gas stream are condensed out. This can give an aqueous phase and an organic phase which are separated in a phase separator. If the product gas stream from the ethane dehydrogenation contains appreciable amounts of water, water is usually removed prior to the direct chlorination so that no aqueous phase is obtained in the condensation step after the direct chlorination. The condensation step is generally carried out at from 80 to 140° C., preferably room temperature, and a pressure of from 3 to 6 bar. Pure 1,2-dichloroethane is isolated from the organic phase, for example in a series of two distillation columns.

The incondensable components of the product gas stream comprise ethane, unreacted ethene, possibly oxygen and/or hydrogen, traces of incompletely condensed chlorinated by-products from the direct chlorination and, if they have not been separated off prior to the direct chlorination, incondensable secondary constituents from the ethane dehydrogenation. The traces of the chlorinated by-products are in the order of from 10 to 10 000 ppm.

In an embodiment of the invention, incondensable secondary constituents from the ethane dehydrogenation are not separated off prior to the direct chlorination and the incondensable components of the product gas stream from the direct chlorination are recirculated as an ethane-containing circulating gas stream to the ethane dehydrogenation. It is possible, as described above, to separate carbon dioxide from the circulating gas stream by means of gas scrubbing, if desired in combination with prior combustion of carbon monoxide.

As a result of the dilution of ethene with unreacted ethane and possibly incondensable secondary constituents in the feed gas stream to the direct chlorination, higher space-time yields and higher selectivities of 1,2-dichloroethane formation are achieved, particularly when a liquid-phase direct chlorination is carried out in a bubble column.

In a preferred embodiment of the process of the present invention, the above-described processes of oxychlorination and direct chlorination are carried out in parallel.

Preference is thus given to a process which comprises the following steps:

(A) feeding an ethane-containing feed gas stream into a dehydrogenation zone and dehydrogenating ethane to ethene to give a product gas stream comprising ethane, ethene and secondary constituents, (B1) feeding a first substream of the ethane- and ethene-containing dehydrogenation product gas stream, optionally after having separated off secondary constituents, into an oxychlorination zone, oxychlorinating ethene to 1,2-dichloroethane to give a product gas stream comprising 1,2-dichloroethane, ethane and possibly further secondary constituents, isolating 1,2-dichloroethane and an ethane-containing circulating gas stream and recirculating the ethane-containing circulating gas stream to the ethane dehydrogenation, (B2) feeding a second substream of the ethane- and ethene-containing dehydrogenation product gas stream, optionally after having separated off secondary constituents, into a direct chlorination zone, directly chlorinating ethene to 1,2-dichloroethane to give a product gas stream comprising 1,2-dichloroethane, ethane and possibly further secondary constituents, isolating 1,2-dichloroethane and an ethane-containing circulating gas stream and recirculating the ethane-containing circulating gas stream to the ethane dehydrogenation.

In a variant of this preferred process, water is firstly separated off from the second substream of the dehydrogenation product gas stream and ethane and ethene are subsequently separated off from the other secondary constituents by means of a high-boiling absorption medium in an absorption/desorption cycle, and ethane and ethene are fed into the direct chlorination zone.

In a further variant of this preferred process, a circulating gas stream comprising ethane and incondensable secondary constituents selected from the group consisting of ethene, oxygen, methane, carbon oxides, nitrogen and hydrogen, possibly together with traces of chlorinated hydrocarbons, is in each case separated off from the product gas stream from the oxychlorination and from the product gas stream from the direct chlorination and is recirculated to the ethane dehydrogenation. These circulating gas streams are preferably combined and subjected to a carbon dioxide gas scrub, if appropriate after carbon monoxide combustion.

In a further variant of this preferred process, a gas stream comprising ethane and incondensable secondary constituents selected from the group consisting of ethene, oxygen, methane, carbon oxides, nitrogen and hydrogen together with traces of organic chlorine compounds is in each case separated off from the product gas stream from the oxychlorination and from the product gas stream from the direct chlorination. From this gas stream, a circulating gas stream which consists essentially of ethane and may also contain traces of organic chlorine compounds is separated off, preferably by means of a high-boiling absorption medium in an absorption/desorption cycle, and is recirculated to the ethane dehydrogenation. The gas streams are preferably combined before the ethane is separated off.

In the variants mentioned, the work-up of the incondensable organic constituents from the oxychlorination and from the direct chlorination is preferably carried out jointly.

Traces of organic chlorine compounds can be separated off from the circulating gas stream in an absorption step using suitable absorption media known to those skilled in the art.

The 1,2-dichloroethane obtained in the oxychlorination and/or direct chlorination of ethene can be subjected to pyrolysis to give vinyl chloride and hydrogen chloride. If an oxychlorination is carried out, the hydrogen chloride formed in the pyrolysis is usually recirculated to the oxychlorination.

The present invention therefore also provides a process for preparing vinyl chloride which starts from ethane as raw material and in which, as described above, an ethane dehydrogenation and an ethene chlorination are carried out and 1,2-dichloroethane obtained is pyrolyzed to give vinyl chloride.

In a particularly preferred embodiment of the process of the present invention, the oxychlorination and the direct chlorination are carried out in parallel, the 1,2-dichloroethane obtained is subjected to a pyrolysis to give vinyl chloride and hydrogen chloride and hydrogen chloride is recirculated to the oxychlorination.

The pyrolysis is carried out in the gas phase, for example at 500° C. and pressures of from 6 to 21 bar.

A product gas stream comprising vinyl chloride, hydrogen chloride, 1,2-dichloroethane and possibly secondary constituents is obtained. Hydrogen chloride and vinyl chloride are separated off from this. Unreacted 1,2-dichloroethane can be returned to the pyrolysis, with crude 1,2-dichloroethane which has been separated off being able to be worked up jointly with crude 1,2-dichloroethane from the oxychlorination and from the direct chlorination to isolate pure 1,2-dichloroethane.

Preference is thus given to a process for preparing vinyl chloride which starts out from ethane as raw material and comprises, as described above, (A) dehydrogenating ethane to ethene, carrying out (B1) an oxychlorination and (B2) a direct chlorination of ethene in parallel and, in a further step (C) feeding 1,2-dichloroethane from the oxychlorination and from the direct chlorination into a pyrolysis zone, pyrolyzing 1,2-dichloroethane to vinyl chloride to give a product gas stream comprising vinyl chloride, hydrogen chloride, 1,2-dichloroethane and possibly secondary constituents, separating off hydrogen chloride and vinyl chloride and recirculating hydrogen chloride to the oxychlorination.

The process of the present invention is illustrated below with reference to the figures.

FIG. 1 shows a flow diagram of one embodiment of the process of the present invention. The ethane-containing feed gas stream 1 is mixed with the ethane-containing circulating gas stream 11, preheated in a heat exchanger 2 to the reactor inlet temperature required and fed into the dehydrogenation reactor 3. Oxygen or air as cofeed 4 and/or hydrogen as cofeed 4b is/are optionally fed into the dehydrogenation reactor 3. Hydrogen chloride 6 and oxygen 6a are mixed into the ethene-containing product gas stream 5 from the dehydrogenation. The gas mixture is brought to the necessary feed temperature in a heat exchanger 7 and fed into the oxychlorination reactor 8. The product gas stream 9 from the oxychlorination is conveyed to a condenser 10 and separated into a gas stream 11 comprising incondensable constituents and a stream 12 comprising condensable constituents. The gas stream 11 comprising the incondensable constituents is recirculated as circulating gas stream to the ethane dehydrogenation. The stream 12 comprising the condensable constituents is separated in a phase separator 13 to give an aqueous phase 14 and an organic phase 15. The aqueous phase is discharged from the process. The organic phase 15 is fractionated in a series of two distillation columns 16 and 17, with a low-boiling fraction 18 being obtained at the top of the first column, a high-boiling fraction 19 being obtained at the bottom of the second column and pure 1,2-dichloroethane 20 being obtained at the top of the second column.

Figure 2:
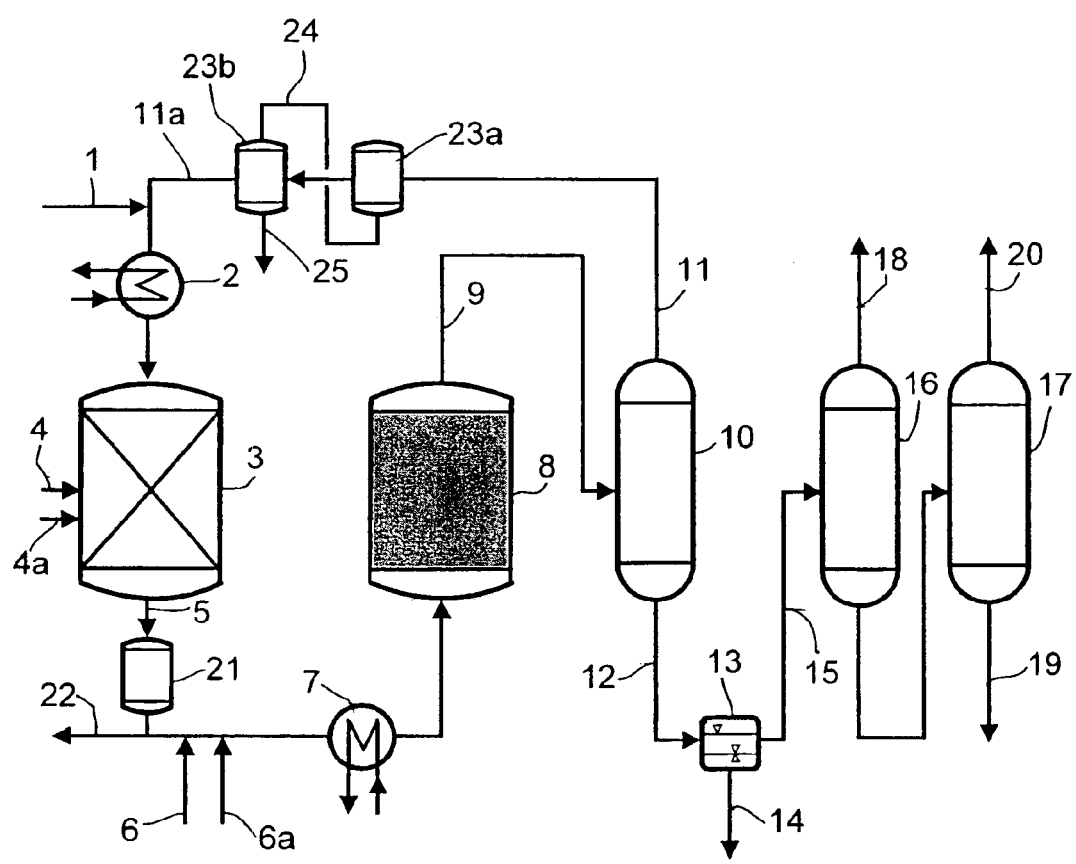

FIG. 2 shows a flow diagram of another embodiment of the process of the present invention. As a difference from the embodiment shown in FIG. 1, hydrogen is selectively oxidized to water in a hydrogen burner 21 installed downstream of the dehydrogenation reactor. If desired, a substream 22 of the gas can be taken off and used as feed gas stream in another process, for example the preparation of ethylene oxide or the preparation of ethylbenzene. An ethane- and ethene-containing circulating gas stream 11a is separated off from the other incondensable constituents 25 in the gas stream 11 comprising the incondensable constituents by means of a circulated high-boiling solvent 24 in an absorption/desorption apparatus 23a,b. The incondensable constituents are discharged from the process.

Figure 3:
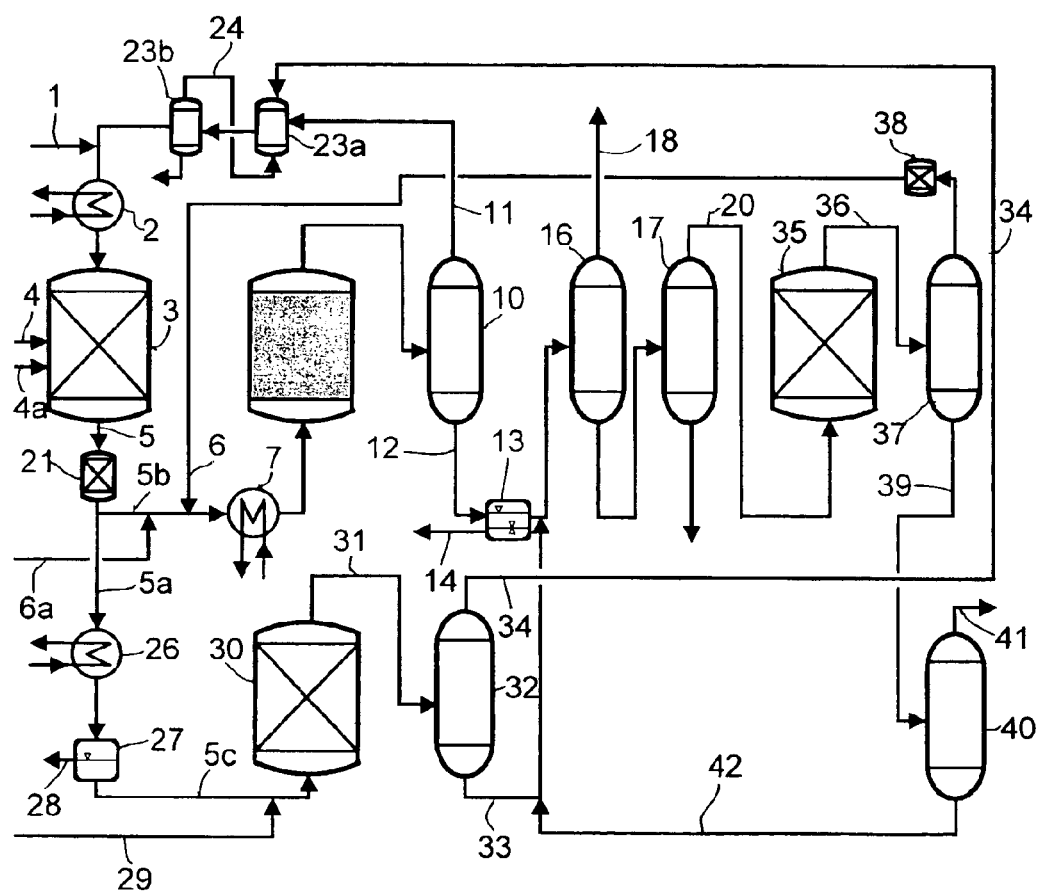

FIG. 3 shows a flow diagram of a further embodiment of the process of the present invention. The product gas stream from the ethane dehydrogenation 5 is divided into two substreams 5a and 5b. The substream 5a is cooled in a heat exchanger 26 and passed to a condenser 27 in which a water stream 28 is condensed out. The essentially water-free gas stream 5c is mixed with a chlorine gas stream 29 and fed into the direct chlorination reactor 30. The product gas stream 31 from the direct chlorination is separated into a gas stream 34 comprising incondensable constituents and a stream 33 comprising condensable constituents in a condenser 32. The stream 33 comprising the condensable constituents is worked up in the distillation columns 16 and 17 together with the stream 15 comprising the condensable organic constituents from the oxychlorination reaction to give pure 1,2-dichloroethane 20. The gas stream 34 comprising the incondensable constituents is passed to the absorption/desorption apparatus 23a,b in which the ethane and ethene are separated from the other incondensable constituents in the gas streams 11 and 34. The 1,2-dichloroethane stream taken off at the top of the second distillation column 17 is fed into the pyrolysis reactor 35. The product gas stream 36 from the 1,2-dichloroethane pyrolysis is passed to a distillation column 37 in which a hydrogen chloride stream is separated off via the top. Any acetylene present in this is hydrogenated in a hydrogenation reactor 38 and the hydrogen chloride stream which has been freed of acetylene is recirculated as gas stream 6 to the oxychlorination. The stream 39 which is obtained at the bottom of the distillation column 37 and comprises the liquid products of the 1,2-dichloroethane pyrolysis is introduced into a distillation column 40. Crude vinyl chloride 41 is obtained at the top of the distillation column 40 and can be purified further. A 1,2-dichloroethane-containing stream 42 is obtained at the bottom of this column and is worked up jointly with the stream 33 comprising the condensable constituents from the direct chlorination and the stream 15 comprising the condensable organic constituents from the oxychlorination in the distillation columns 16 and 17.

We claim:

1. A process for preparing 1,2-dichloroethane, which comprises (A) feeding an ethane-containing feed gas stream into a dehydrogenation zone and dehydrogenating ethane to ethene to give a product gas stream comprising ethane, ethene and secondary constituents, (B1) feeding a first substream of the ethane- and ethene-containing dehydrogenation product gas stream, optionally after having separated off secondary constituents, into an oxychlorination zone, oxychlorinating ethene to 1,2-dichloroethane to give a product gas stream comprising 1,2-dichloroethane, ethane and possibly further secondary constituents, isolating 1,2-dichloroethane and an ethane-containing circulating gas stream and recirculating the ethane-containing circulating gas stream to the ethane dehydrogenation, (B2) feeding a second substream of the ethane- and ethene-containing dehydrogenation product gas stream, optionally after having separated off secondary constituents, into a direct chlorination zone, directly chlorinating ethene to 1,2-dichloroethane to give a product gas stream comprising 1,2-dichloroethane, ethane and possibly further secondary constituents, isolating 1,2-dichloroethane and an ethane-containing circulating gas stream and recirculating the ethane-containing circulating gas stream to the ethane dehydrogenation, (C) feeding 1,2-dichloroethane from the oxychlorination and from the direct chlorination into a pyrolysis zone, pyrolyzing 1,2-dichloroethane to vinyl chloride to give a product gas stream comprising vinyl chloride, hydrogen chloride, 1,2-dichloroethane and possibly secondary constituents, isolating vinyl chloride and recirculating hydrogen chloride to the oxychlorination.

2. A process as claimed in claim 1, wherein the dehydrogenation (step A) is carried out by thermal cracking, oxidative dehydrogenation or nonoxidative catalytic dehydrogenation.

3. A process as claimed in claim 2, wherein the dehydrogenation is carried out by autothermal catalytic dehydrogenation.

4. A process as claimed in any of claims 1 to 3, wherein water is firstly separated off from the second substream of the dehydrogenation product gas stream and ethane and ethene are subsequently separated off from the other secondary constituents by means of a high-boiling absorption medium in an absorption/desorption cycle, and ethane and ethene are fed into the direct chlorination zone.

5. A process as claimed in any of claims 1 to 4, wherein a circulating gas stream comprising ethane and incondensable secondary constituents selected from the group consisting of ethene, methane, carbon oxides, nitrogen and hydrogen is separated off from the product gas stream from the oxychlorination and is recirculated to the ethane dehydrogenation.

6. A process as claimed in any of claims 1 to 5, wherein a gas stream comprising ethane and incondensable secondary constituents selected from the group consisting of ethene, methane, carbon oxides, nitrogen and hydrogen is separated off from the product gas stream from the oxychlorination, a circulating gas stream consisting essentially of ethane is separated off from this gas stream by means of a high-boiling absorption medium in an absorption/desorption cycle and this circulating gas stream is recirculated to the ethane dehydrogenation stage.

7. A process as claimed in any of claims 1 to 3, wherein a circulating gas stream comprising ethane and incondensable secondary constituents selected from the group consisting of ethene, methane, carbon oxides, nitrogen and hydrogen is in each case separated off from the product gas stream from the oxychlorination and from the product gas stream from the direct chlorination and is recirculated to the ethane dehydrogenation.

8. A process as claimed in claim 5 or 7, wherein carbon dioxide is removed from the circulating gas stream by means of a carbon dioxide gas scrub.

9. A process as claimed in claim 8, wherein carbon monoxide is oxidized to carbon dioxide in an upstream combustion stage.

10. A process as claimed in any of claims 1 to 3, wherein a gas stream comprising ethane and incondensable secondary constituents selected from the group consisting of ethene, methane, carbon oxides, nitrogen and hydrogen is in each case separated off from the product gas stream from the oxychlorination and from the product gas stream from the direct chlorination, a gas stream consisting essentially of ethane is separated off from this gas stream by means of a high-boiling absorption medium in an absorption/desorption cycle and this gas stream consisting essentially of ethane is recirculated as circulating gas stream to the ethane dehydrogenation.

* * * * *